United States Patent [19]

Watanabe

[11] Patent Number: 4,889,106
[45] Date of Patent: Dec. 26, 1989

[54] TREATING INSTRUMENT FOR ENDOSCOPE

[75] Inventor: Yoshio Watanabe, Kawaguchi, Japan

[73] Assignee: Kabushiki Kaisha Machida Seisakusho, Tokyo, Japan

[21] Appl. No.: 268,707

[22] Filed: Nov. 8, 1988

[30] Foreign Application Priority Data

Nov. 13, 1987 [JP] Japan ............... 62-172603[U]

[51] Int. Cl.⁴ .................... A63B 1/00; A46B 5/00
[52] U.S. Cl. .......................... 128/4; 15/143 R
[58] Field of Search ............ 128/4, 6; 15/143 R, 15/206; 248/110, 111; 40/330

[56] References Cited

U.S. PATENT DOCUMENTS

| | | | |
|---|---|---|---|
| 1,515,503 | 11/1924 | Lucey | 15/206 |
| 2,159,322 | 5/1939 | Drummond | 40/330 X |
| 4,336,794 | 6/1982 | Chikama | 128/4 |
| 4,771,766 | 9/1988 | Aoshiro et al. | 128/4 |

FOREIGN PATENT DOCUMENTS 62-14809  4/1987  Japan.
62-19172  4/1987  Japan.

*Primary Examiner*—William H. Grieb
*Attorney, Agent, or Firm*—Wegner & Bretschneider

[57] ABSTRACT

A treating instrument for an endoscope comprises an elongated body, an acting unit provided at a forward end of the body, and a ring portion provided at a proximal end of the body. The ring portion is adapted to be hung on a peg to suspend the treating instrument from the peg. The ring portion is formed with a cut-out permitting the peg to pass through the cut-out. The ring portion has a top located remotest from the proximal end of the body. The cut-out is formed at a location remote from a top of the ring portion.

6 Claims, 2 Drawing Sheets

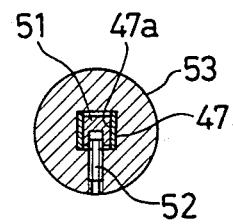
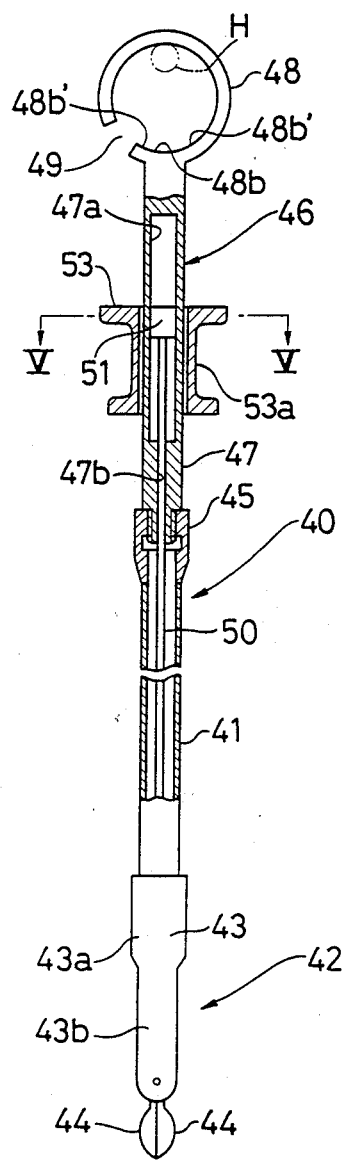
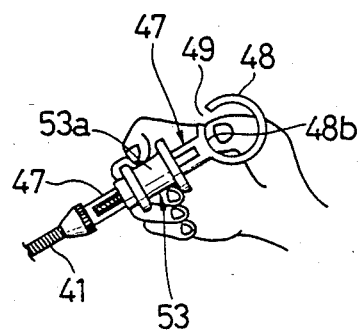

TREATING INSTRUMENT FOR ENDOSCOPE

BACKGROUND OF THE INVENTION

The present invention relates to a treating instrument for an endoscope and, more particularly, to an improvement in a support structure for suspending the treating instrument from a peg.

An endoscope is known well as an instrument for observing a body cavity or a coelom in a human body. A treating instrument is also known well, which is inserted in and extends through a guide channel formed in the endoscope to execute a certain action with respect to a wall surface of the body cavity. As disclosed in Japanese Patent Publication No. 62-19172 and Japanese Utility Model Publication No. 62-14809, the treating instrument comprises an elongated body so designed as to extend through the channel in the endoscope. The body is provided at its forward end with an acting unit. The acting unit includes, for example, a forceps for cutting out the affected part on the wall surface of the body cavity to collect cells of the affected part for the purpose of inspection, or a brush for collecting cells of the affected part.

A ring portion is formed at the proximal end of the body. The ring portion is used for manipulating the acting unit of the treating instrument generally in such a manner that one finger of an operator is inserted in the ring portion, or that the ring portion is held between two fingers. As disclosed in the above Japanese Patent Publication No. 62-19172, the ring portion is also effective for use in storing the treating instrument. That is, the ring portion is hung on an elongated peg projecting horizontally from a wall such that the peg is inserted into the ring portion, whereby the treating instrument can be suspended from the peg.

In the treating instrument constructed as above, the ring portion to be hung on the peg is formed into a completely closed loop. Accordingly, when it is desired to remove the treating instrument from the peg, it is required that the ring portion is first moved along the peg and then is taken out from the forward end of the peg. By this reason, there is the following inconvenience. That is, in case where a plurality of treating instruments are suspended from the peg, if it is desired to remove, from the peg, the rearmost treating instrument located adjacent the rearward end of the peg or adjacent the wall, the remaining treating instruments must be removed, together with the rearmost treating instrument, from the peg. Moreover, the remaining treating instruments not expected to be used must again be suspended from the peg. In this manner, the removing operation of the treating instrument is troublesome, and it takes a long time for the removing operation. Further, if the remaining treating instruments are many in number, one or more treating instruments may erroneously be dropped when the remaining treating instruments are removed from and again suspended from the peg.

SUMMARY OF THE INVENTION

It is an object of the invention to provide a treating instrument for an endoscope, in which a ring portion can be taken out from an elongated peg in a direction crossing a longitudinal axis of the peg, thereby facilitating removal operation of the treating instrument from the peg.

According to the invention, there is provided a treating instrument for an endoscope, comprising:

(a) an elongated body having a forward end and a proximal end;

(b) an acting unit provided at the forward end of the body;

(c) a ring portion provided at the proximal end of the body, the ring portion being adapted to be hung on a peg to suspend the treating instrument from the peg, the ring portion being formed with a cut-out permitting the peg to pass through the cut-out, the ring portion having a top thereof located remotest from the proximal end of the body, the cut-out being formed at a location remote from the top of the ring portion.

BRIEF DESCRIPTION OF THE DRAWINGS

FIG. 4 is a partially cross-sectional front elevational view of a treating instrument according to another embodiment of the invention;

FIG. 5 is a cross-sectional view taken along the line V—V in FIG. 4; and

FIG. 6 is a view showing the treating instrument illustrated in FIG. 4, which is manipulated by the right hand of an operator.

DETAILED DESCRIPTION

Figure 1:
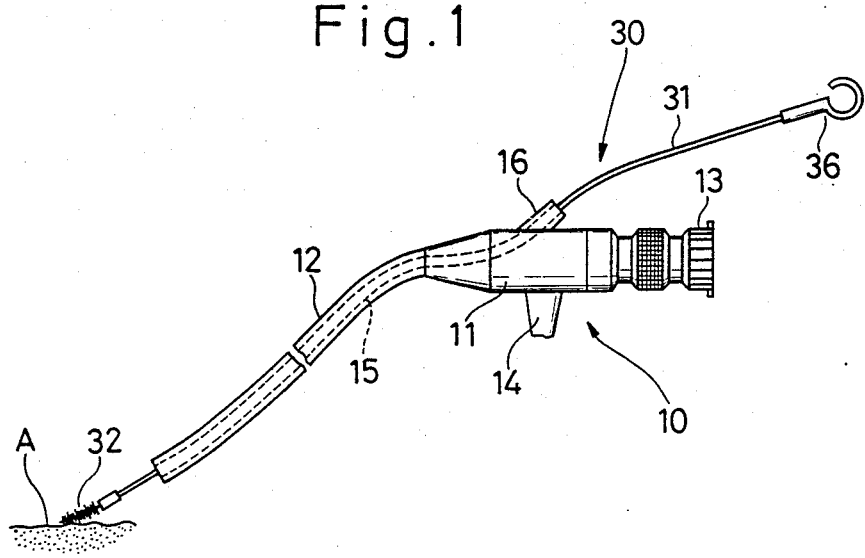
FIG. 1 is a side elevational view of an endoscope and a treating instrument according to an embodiment of the invention.
Figure 2:
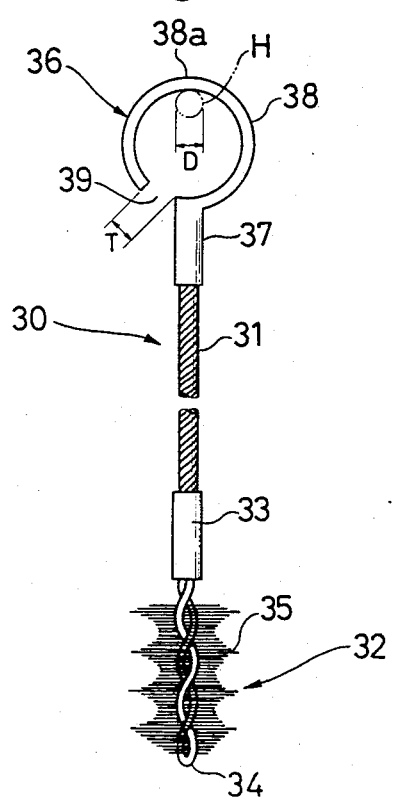
FIG. 2 is an enlarged front elevational view of the treating instrument illustrated in FIG. 1.
Figure 3:
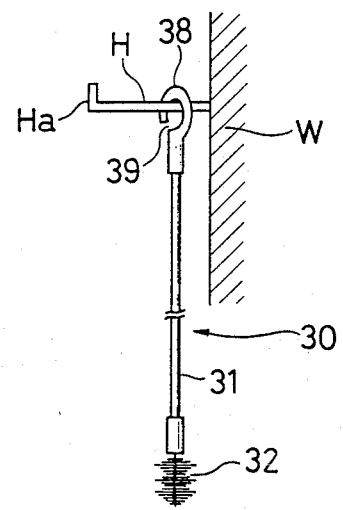
FIG. 3 is a view showing the treating instrument illustrated in FIGS. 1 and 2, which is suspended from an elongated peg.

Referring first to FIGS. 1 through 3, there is shown an endoscope generally designated by the reference numeral 10. The endoscope 10 is known per se, and the construction of the endoscope 10 will briefly be described. The endoscope 10 comprises an operating body 11, a flexible inserting portion 12 extending from one end of the operating body 11, and an ocular portion 13 provided at the other end of the operating body 11. The inserting portion 12 has a forward end section formed hard. The forward end section has an end face formed therein with an illuminating window and a viewing window (both not shown). The illuminating window is optically connected to a light source through an optical fiber bundle (not shown). The optical fiber bundle extends through the inserting portion 12, the operating body 11 and a cable 14 which extends from the operating body 11. The viewing window is optically connected to the ocular portion 13 through an image transmitting system (not shown) including an optical fiber bundle.

Incorporated in the endoscope 10 is a guide channel 15 which is formed by a flexible tube and which extends through the operating body 11 and the inserting portion 12. The guide channel 15 has one end thereof which opens to the end face of the hard forward end section of the inserting portion 12. The other end of the guide channel 15 is connected to a guide tube section 16 which projects from the operating body 11.

A treating instrument 30 for use with the endoscope 10 comprises, as shown in FIG. 2, an elongated flexible body 31 made of twisted wires. The body 31 is provided at its forward end with a brush 32 serving as an acting unit. The brush 32 is composed of a tubular holder 33 having one end in which the forward end of the body 31 is fixedly inserted. A twisted retaining wire 34 has opposite ends which are fixedly inserted in the other end of the holder 33. A multiplicity of bristles 35 are held by the retaining wire 34.

A holder 36 formed of rigid resinous material is connected to the proximal end of the body 31. The holder 36 is composed of a tubular shank portion 37 having one end thereof in which the proximal end of the body 31 is fixedly inserted, and a circular ring portion 38 formed integrally at the other end of the shank portion 37.

The ring portion 38 is provided therein with a cut-out 39 which is located remote from a top 38a of the ring portion 38 which is located remotest from the other end of the shank portion 37. It is particularly preferable that the cut-out 39 is formed in a part of a half of the ring portion 38 on the side of the body 31. In the embodiment illustrated in FIGS. 1 and 2, the cut-out 39 is formed immediately adjacent the other end of the shank portion 37.

The cut-out 39 has a width T which is larger than a diameter D of a peg H to be described later, in order to permit the peg H to pass through the cut-out 39.

The treating instrument 30 constructed as above is so designed as to be used with the endoscope 10, as shown in FIG. 1. Specifically, the treating instrument 30 is inserted into the guide channel 15 through the guide tube section 16. FIG. 1 shows a state in which the inserting operation of the treating instrument 30 has been completed. In this state, the body 31 extends through the guide channel 15; the brush 32 at the forward end of the body 31 projects from the forward end of the inserting portion 12 and is located within the body cavity; and the holder 36 at the proximal end of the body 31 is remote from the guide tube section 16 and is located on the outside of the body cavity. With a finger of an operator inserted into the ring portion 38 of the holder 36, or with the ring portion 38 clamped between two fingers, the holder 36 is pushed and pulled along the axis of the body 31, whereby the brush 32 rubs the affected part A on a wall surface defining the body cavity, to collect tissue of the affected part A.

The above treating instrument 30 is washed and sterilized and, subsequently, is suspended from the peg H fixedly mounted to a wall W, as shown in FIG. 3. Specifically, the peg H is formed into an elongated shape and extends horizontally. The peg H has a forward end Ha bent upwardly. The ring portion 38 is hung on the peg H in such a manner that the peg H passes through the cut-out 39 in the ring portion 38 of the treating instrument 30. In the state in which the treating instrument 30 is suspended from the peg H, the peg H is abutted against a lower surface of the top 38a of the ring section 38, as shown in FIG. 2.

When the treating instrument 30 is used again, the ring portion 38 is removed from the peg H in such a manner that the peg H passes through the cut-out 39. In this manner, hanging and removal of the ring portion 38 on and from the peg H can be effected in a direction crossing the longitudinal axis of the peg H, without the ring portion 38 being moved along the longitudinal axis of the peg H. Accordingly, when the specific treating instrument 30 is removed from the peg H in case where a plurality of remaining treating instruments are suspended from the same peg H on the side of the forward end Ha thereof, it is not required for the remaining treating instruments to be removed from and again suspended from the peg H. Thus, the removing operation can be facilitated. Moreover, since it is unnecessary to move the remaining treating instruments along the peg H, it is possible to prevent a falling accident of one or more of the remaining treating instruments, which is anticipated when the treating instrument 30 is removed from the peg H in case where the remaining treating instruments are many in number.

Referring to FIGS. 4 through 6, there is shown a treating instrument generally designated by the reference numeral 40, according to another embodiment of the invention. The treating instrument 40 has a body 41 made of an elongated flexible tube. The body 41 is formed by, for example, wires wound helically. The body 41 is provided at its forward end with a forceps unit 42 serving as an acting unit. The forceps unit 42 has a holder 43 which is composed of a tubular portion 43a and a pair of opposed arms 43b (only one shown) extending from the tubular portion 43a. The forward end of the body 41 is fixedly inserted in the tubular portion 43a of the holder 43. A pair of bowl-shaped cutter blades 44 and 44 are connected pivotally to the forward ends of the arms 43b for angular movement toward and away from each other.

On the other hand, an attaching nut 45 is fixedly mounted to the proximal end of the body 41 by means of brazing or the like. A holder 46 formed of hard resinous material is fixedly mounted to the proximal end of the body 41 through the attaching nut 45. The holder 46 is composed of a shank portion 47 whose one end is threadedly engaged with and fixed to the attaching nut 46, and a ring portion 48 integrally formed at the other end of the shank portion 47.

The shank portion 47 has a rectangular cross-sectional shape, and has a guide bore 47a extending longitudinally. As shown in FIG. 5, the guide bore 47a opens to a pair of opposed side faces of the shank portion 47. The shank portion 47 is formed therein with an inserting bore 47b extending longitudinally of the shank portion 47. The inserting bore 47b has one end thereof communicating with the guide bore 47a. The other end of the inserting bore 47b opens to an end face of the one end of the shank portion 47.

The ring portion 48 is circular in shape, and is formed with a cut-out 49 to permit the peg H to pass through the cut-out 49, similarly to the previous embodiment. In the embodiment illustrated in FIG. 4, the cut-out 49 is formed in a half of the ring portion 48 on the side of the shank portion 47 and at a location spaced slightly away from the other end of the shank portion 47. Thus, the ring portion 48 is formed with a receiving section 48b for receiving manipulating force from the finger of the operator, in the vicinity of the other end of the shank portion 47. The receiving section 48b is provided with pair of arcuate regions 48b' and 48b' extending from the other end of the shank portion 47 in their respective directions opposite to each other.

A wire 50 extends through the body 41. One end of the wire 50 is connected to the cutter blades 44 and 44 of the forceps unit 42 through a link mechanism (not shown). The other end of the wire 50 extends to the guide bore 47a through the inserting bore 47b formed in the shank portion 47. A slider 51 is fixedly connected to the other end of the wire 50. The slider 51 is accommodated in the guide bore 47a for sliding movement along an axis of the guide bore 47a. As shown in FIG. 5, the slider 51 is connected, through a screw 52, to a moving block 53 formed of hard resinous material. The moving block 53 is tubular in shape and is fitted about the shank portion 47 for sliding movement therealong. The moving block 53 is formed with an annular groove 53a.

The treating instrument 40 constructed as above is inserted in and extends through the channel 15 of the endoscope 10 (see FIG. 1) in a manner similar to that of the treating instrument 30 illustrated in FIGS. 1 through 3. With the treating instrument 40 extending through the channel 15, the forceps unit 42 is arranged within the body cavity, while the holder 46 is arranged on the outside of the body cavity. An operator manipulates the treating instrument 40 in a manner shown in FIG. 6. Specifically, the operator applies the middle finger and the forefinger of his right hand to the annular groove 53a of the moving block 53, and inserts the thumb into the ring portion 48 of the holder 46. When the moving block 53 is moved along the shank portion 47 of the holder 46 away from the ring portion 48, the movement is transmitted to the link mechanism of the forceps unit 42 through the wire 50, to move the cutter blades 44 and 44 angularly away from each other. Subsequently, the cutter blades 44 and 44 are moved toward the affected part.

The moving block 53 is then moved toward the ring portion 48, whereby the cutter blades 44 and 44 of the forceps unit 42 are moved angularly toward each other. At this time, tissue of the affected part is resected by the cutter blades 44 and 44 from the affected part. When the blades 44 and 44 are moved angularly toward each other, force from the thumb acts upon the receiving section 48b of the ring portion 48. In this connection, the receiving section 48b is provided with the pair of arcuate regions 48b and 48b and coincides with the configuration of the thumb. Thus, it is ensured that the receiving section 38b receives the force from the thumb, making it possible to facilitate manipulation of the treating instrument 40.

When it is desired to store the treating instrument 40, the ring section 48 is hung on the peg H such that the peg H passes through the cut-out 49 of the ring portion 48.

If the diameter of the ring portion 48 is brought into coincidence with the diameter of the thumb, manipulation can be made more easy and reliable, because no play is left between the thumb and the ring portion 48. In this case, even if the thumb is different in diameter from operator to operator, the ring portion 48 can be fitted to the thumb, because the ring portion 48 is formed with the cut-out 49 and can be deformed elastically.

It is understood that the invention is not limited to the above-described embodiments, but various modifications can be made to the invention. For example, in the treating instrument constructed as shown in FIG. 4, a brush serving as an acting unit may be mounted to the forward end of the wire 50, in place of the forceps unit 42 mounted to the body 41. In this case, movement of the moving block 53 enables the brush to be moved between a position where the brush is retracted into the body 41 and a position where the brush projects from the body 41.

Further, the invention is applicable to a treating instrument provided, as an acting unit, with a brush for washing the guide channel in the endoscope, and to any other suitable treating instruments for the endoscope.

What is claimed is:

1. A treating instrument for an endoscope, comprising:
   (a) an elongated body having a forward end and a proximal end;
   (b) an acting unit provided at the forward end of said body;
   (c) a ring portion provided at said proximal end of said body, said ring portion being adapted to receive an operator's finger, said ring portion also being adapted to be hung on a peg to suspend the treating instrument from said peg, said ring portion being formed with a cut-out permitting said peg to pass through said cut-out, and said ring portion having a top located remotest from said proximal end of said body, said cut-out being formed at a location remote from said top of said ring portion.

2. A treating instrument according to claim 1, wherein said cut-out is formed in a part of a half of said ring portion on the side of said body.

3. A treating instrument according to claim 2, further comprising a holder including a shank portion having one end thereof connected to the proximal end of said body, and said ring portion formed at the other end of said shank portion.

4. A treating instrument according to claim 3, wherein said ring portion is circular in shape.

5. A treating instrument according to claim 4, wherein said cut-out in said ring portion is formed immediately adjacent the other end of said shank portion.

6. A treating instrument according to claim 4, wherein said cut-out in said ring portion is formed at a location remote from the other end of said shank portion, said ring portion being provided, in the vicinity of the other end of said shank portion, with a receiving section for receiving manipulating force from a finger of an operator, said receiving section having a pair of arcuate regions which extend from the other end of said shank portion in their respective directions opposite to each other.

* * * * *